United States Patent [19]

Owsley et al.

[11] 4,076,758

[45] Feb. 28, 1978

[54] SYNTHESIS OF VICINAL GLYCOLS

[75] Inventors: Dennis C. Owsley, St. Louis; Jordan J. Bloomfield, Creve Coeur, both of Mo.

[73] Assignee: Monsanto Company, St. Louis, Mo.

[21] Appl. No.: 749,127

[22] Filed: Dec. 9, 1976

[51] Int. Cl.$^2$ .................. C07C 29/00; C07C 31/14
[52] U.S. Cl. ................. 260/618 R; 260/448.8 R; 260/635 R
[58] Field of Search ............. 260/635 R, 448.8 R, 260/618 R

[56] References Cited

U.S. PATENT DOCUMENTS 3,076,846    2/1963    McClellan ............... 260/635 R

OTHER PUBLICATIONS

Noll, "Chemistry and Technology of Silicones", (1968), pp. 230, 371.
Sommer, "Stereochemistry, Mechanism and Silocon", Chapter 8, pp. 131–133.
Schwetlick, et al., "Angew. Chem.", vol. 72, (1960), pp. 779–780.
Ladygin, et al., "Kinetics and Catalysis", vol. 6, (1965), pp. 189–195, vol. 7, (1966), pp. 832–839, Translations from the Russian.

*Primary Examiner*—Joseph E. Evans
*Attorney, Agent, or Firm*—Scott J. Meyer; John D. Upham

[57] ABSTRACT

Relatively low molecular weight primary alcohols are coupled to form relatively higher molecular weight vicinal glycols in which a trialkylsilyl protecting group is employed on the hydroxyl position of said low molecular weight primary alcohol during said coupling reaction.

18 Claims, No Drawings

SYNTHESIS OF VICINAL GLYCOLS

BACKGROUND OF THE INVENTION

This invention relates to the production of vicinal glycols from starting molecules having fewer carbon atoms such as, for example, the preparation of ethylene glycol and glycerol from methanol. More particularly, this invention is concerned with the coupling of relatively low molecular weight or short chain primary alcohols to form relatively higher molecular weight or vicinal glycols by employing a trialkylsilyl protecting group on the hydroxyl position of said low molecular weight primary alcohol.

In view of the fuel and mineral shortages facing the world, particularly petroleum feedstocks, there is a scarcity of vital building blocks such as ethylene and propylene used to synthesize many modern chemical entities. Consequently, alternate carbon sources for the chemical industry's basic organic chemicals must be developed for future needs from either coal or single carbon molecules such as carbon monoxide, carbon dioxide or methanol.

Two major products produced from petroleum-derived feedstocks such as ethylene and propylene are, respectively, ethylene glycol and glycerol. Ethylene glycol is widely used for antifreeze and in numerous nonantifreeze outlets, including cellophane, polyester fibers and films, and polyglycols. Glycerol finds wide use in cosmetics, dentifrices, drugs and pharmaceuticals, alkyd resins, cellophane and in tobacco as a humectant and in the manufacture of plasticizers for cellulose cigarette filters.

In the production of ethylene glycol, ethylene oxide is usually first prepared by direct oxidation of ethylene or by the chlorohydrin synthesis and the ethylene oxide is then reacted with water to make ethylene glycol.

Although glycerol is a natural by-product of soap manufacture, a significant quantity of synthetic glycerin also is prepared from propylene. One such process involves the chlorination of propylene to allyl chloride, conversion into epichlorohydrin, and thence into glycerin. Another process involves oxidation of propylene to acrolein, conversion into allyl alcohol, then reaction with hydrogen peroxide to yield glycerin. In a third process, propylene oxide is catalytically converted into allyl alcohol, which is treated with peracetic acid to yield glycidol. Glycidol then combines with water to make glycerin.

An improved method of producing vicinal glycols such as, for example, ethylene glycol and glycerol, from shorter chain molecules such as, for example, methanol, instead of employing petroleum-derived feedstocks such as ethylene and propylene, would provide significant advantages over prior methods of production.

BRIEF DESCRIPTION OF THE INVENTION

In accordance with the present invention, vicinal glycols are produced from starting molecules having fewer carbon atoms. In particular, relatively low molecular weight or short chain primary alcohols are coupled to form relatively higher molecular weight vicinal glycols by employing a trialkylsilyl protecting group on the hydroxyl position of said low molecular weight primary alcohol.

As used herein, the term "trialkylsilyl" means a group containing a silicon atom bonded to three alkyl radicals, any of which can be the same as, or different than, any other.

The process of this invention involves the oxidative or dehydrogenative coupling of the shorter chain primary alcohol without over-oxidation to undesirable by-products, for example, aldehydes. The initial dehydrogenation of the shorter chain primary alcohol is thus made to take place on the carbon rather than the hydroxyl group by using the trialkylsilyl blocking group on the hydroxyl. Alcoholysis of the coupled reaction product then readily yields the desired vicinal glycol.

The coupling reaction of this invention is briefly illustrated by the preparation of ethylene glycol and glycerol from methanol. In order to produce ethylene glycol, two trialkylsilyl blocked methanol molecules are reacted to form 1,2-bis(trialkylsiloxy)ethane which, upon methanolysis, yields ethylene glycol. In order to produce glycerol, three trialkylsilyl blocked methanol molecules are reacted to form 1,2,3-tris(trialkylsiloxy)propane which, upon methanolysis, yields glycerol.

The above process has definite advantages over the direct coupling of methanol to ethylene glycol and glycerol. This process has a higher selectivity for ethylene glycol and glycerol and less by-product is produced. That the direct coupling of methanol undesirably leads to a substantial amount of formaldehyde is seen from the work of Schwetlich et al, *Angew. Chem.* 72, 779 (1960); and Ladygin and Saraeva, *Kinetics and Catalysis* 6, 189–95 (1965) and 7, 832–39 (1966).

DETAILED DESCRIPTION OF THE INVENTION

The present invention can be described in greater detail by the following illustrative general reaction equations for the production of ethylene glycol and glycerol, respectively, from methanol:

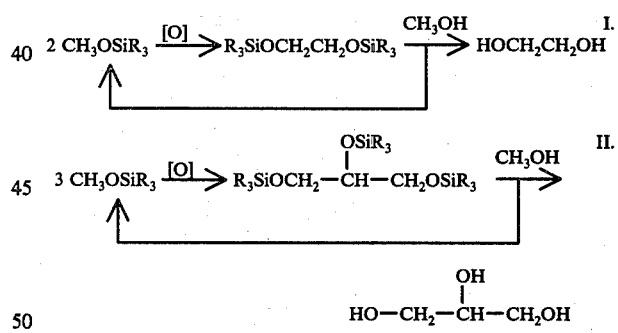

wherein each $R = C_{1-4}$ alkyl, preferably methyl.

The trialkylsilyl blocked methanol molecules used in the foregoing reactions can be initially prepared by reacting anhydrous methanol with metallic sodium in a solvent such as, for example, xylene, adding chlorotrialkylsilane to the mixture and distilling off the desired methoxytrialkylsilane.

The resulting methoxytrialkylsilane can then be reacted under coupling reaction conditions to form the longer chain trialkylsilyl derivatives of the starting alcohol. For example, heating at elevated temperatures in the presence of organic peroxides promotes a free radical coupling reaction. Dialkyl peroxides such as di-t-butyl peroxide are preferred peroxides for use in the free radical coupling reaction. A temperature ranging from about 110° C to about 180° C and preferably about 145° C is employed.

Use of from about one to about 15 mol. % and preferably about 10 mol. % of the peroxide relative to the methoxytrialkylsilane is generally suitable in the coupling reaction.

Although the coupled intermediates are known compounds, they are not known to be prepared by the coupling reaction of this invention. Thus, the 1,2-bis(trialkylsiloxy)ethane has been prepared heretofore by Sprung and Nelson, *J. Org. Chem.* 20, 1750–56 (1955); Langer et al, *J. Org. Chem.* 23, 50–58 (1958); and Fuchs et al, *Tetrahedron* 30 (3), 437–44 (1974). The 1,2,3-tris(trialkylsiloxy)propane has been prepared heretofore by Breederveld et al, *Rec. trav. chim.* 72, 706–10 (1953); and by Sprung and Nelson, supra. In these published procedures, the alcohol moiety of the trialkylsilyl derivative has the same carbon backbone chain length as the starting alcohol. For example, the 1,2-bis(trialkylsiloxy)ethane is prepared from ethylene glycol and the 1,2,3-tris(trialkylsiloxy)propane is prepared from glycerol, rather than from the shorter chain methanol as in the present invention.

Following the preparation of the coupled intermediates, the desired vicinal glycols can be formed by alcoholysis with an appropriate alcohol, for example, by methanolysis to produce ethylene glycol or glycerol. The methoxytrialkylsilane co-product produced in the methanolysis reaction can then be recycled for further use in the initial coupling reaction.

Although in the foregoing detailed description the invention is illustrated by specific reference to the production of ethylene glycol and glycerol from the starting shorter chain primary alcohol, methanol, it will be appreciated that other starting primary alcohols similarly can be used in the coupling reaction to yield higher molecular weight vicinal glycols. Thus, other alkanols such as, for example, ethanol and n-propyl alcohol can be used in place of methanol. Similarly, aralkyl alcohols such as, for example, benzyl alcohol can be used as the starting alcohol to produce higher molecular weight vicinal glycols. To illustrate, the ethanol can be converted to 2,3-butanediol and the benzyl alcohol can be converted to hydrobenzoin by use of the trialkylsilyl blocking group in the coupling reaction.

The following detailed specific examples will still further illustrate the invention although the invention is not limited to these specific examples or to the specific details therein.

EXAMPLE 1

Methoxytrimethylsilane. To 55.2 grams (2.4 g-atom) of sodium under nitrogen in a 2-liter, 3-necked round bottomed flask fitted with addition funnel, Hershberg stirrer, reflux condenser and nitrogen pad was added one liter of xylene. A coarse sodium dispersion was prepared by first heating the mixture until the sodium melted and then rapidly stirring to break up the molten sodium. The flask was cooled to room temperature and 90 ml (about 2.2 mol) of anhydrous methanol was added. When all signs of gas evolution stopped, 217.2 g (2.0 mol) of chlorotrimethylsilane was added over 3 hours. The mixture was stirred overnight (> 12 hours) at room temperature (about 20°–25° C). After the reflux condenser was replaced by a Claisen head condenser, the product was distilled off (bp 45°–58° C) under nitrogen. The product was redistilled through a 3 foot length Vigreaux column under nitrogen to yield 129 g (1.24 mol, 62%) of methoxytrimethylsilane, bp 57°–58° C.

EXAMPLE 2

Ethoxytrimethylsilane was prepared by using the same procedure as in Example 1 and substituting ethanol for an equimolar amount of methanol in said procedure.

EXAMPLE 3

Coupling of methoxytrimethylsilane. To a 300 ml Parr stirred autoclave was added 26.0 g (250 mmol) of methoxytrimethylsilane (as produced in Example 1) and 3.0 g (25 mmol) of di-t-butylperoxide. The autoclave was pressured to 200 psig with nitrogen and heated at 145° C for 16 hours, cooled, and the products were analyzed by GLC. GLC analyses were carried out on a Varian Model 2800 gas chromatograph using a 10 foot × 1/16 inch 3% SE-30 on Chrom W column programmed from 75° (isothermal for one minute) to 260° at 10°/minute. At a flow rate of 12 ml/min, retention times were: ethleneglycol-bis-trimethylsilyl ether, 3.8 min; dodecane (internal standard), 7.5 min; and glycerol-tris-trimethylsilyl ether, 8.5 min. A third component (< 2%) had a retention time of 14 min. The yield of ethylene glycol bis-trimethylsilyl ether was 11.6 mmol (46%), while that of the glycerol derivative was 1.7 mmol (10%).

A second reaction, identical to the foregoing, was worked up to isolate ethylene glycol. Methoxytrimethylsilane was distilled from the reaction mixture and methanol was added to the residue. The mixture was brought to reflux and the methoxytrimethylsilane was slowly distilled off. The syrupy residue was treated with a mixture of benzoyl chloride and pyridine (Shriner et al, "Systematic Identification of Organic Compounds," 5th ed., John Wiley and Sons, New York, N.Y. 1964, pp. 246–47). The isolated solid was recrystallized from methanol-water to yield ethylene glycol dibenzoate, mp 71.6°–72° C. The mixture melting point with an authentic sample showed no depression. The NMR spectra (nuclear magnetic resonance) of the two samples were superimposable.

EXAMPLE 4

Coupling of ethoxytrimethylsilane. Ethoxytrimethylsilane (82 g, 750 mmol) (as produced in Example 2) and di-t-butyl peroxide (11 g, 75 mmol) were combined in the 300 ml Parr autoclave and stirred and heated at 145° C for 16 hours. The autoclave was then cooled and the reaction mixture was distilled to recover unreacted starting material. The residue was distilled on a 6 inch Vigreaux column to yield 7.4 g (32 mmol, 43%) of a 1:1 mixture of meso and dl-2,3-butane-diol-bis-trimethylsilylether (bp 36° C/10 mm) and 2.4 g of a higher boiling mixture of several components (bp 95°–105° C/10 mm).

The dimer fraction was shown to be a 1:1 meso and dl mixture by GLC (6 foot × ¼ inch 3% SE-30 on Chrom W, 100° C) and by the NMR spectrum of the dioxolanes prepared from the diols and formaldehyde (Gianni et al, *J. Phys. Chem.* 74, 210 (1970).

The higher boiling mixture had a NMR spectrum consistent with a trimer of ethoxymethylsilane. Its mass spectrum had intense peaks at 117 and 233 amu [$CH_3^+CHOSiMe_3$ and $CH_3CH(OSiMe_3)$—$(CH_3)(OSiMe_3)^+$] but no molecular ion at 350 amu. An ion at 348 amu was detected which corresponds to a trimer less two hydrogen atoms. The higher boiling component of the coupling reaction was therefore assigned the structures of a mixture of saturated and unsaturated trimers of ethoxytrimethylsilane (6.8 mmol, 14%).

2,3-butanediol can be prepared from the foregoing 2,3-butane-diol-bis-trimethylsilyl ether by ethanolysis at refluxing temperature in a manner similar to the methanolysis procedure of Example 3 for the production of ethylene glycol.

EXAMPLE 5

Coupling of Benzyloxytrimethysilane. To 18.1 g (100 mmol) of benzyloxytrimethylsilane (prepared as in Pierce "Silylation of Organic Compounds", Pierce Chemical Co., Rockford Ill. 1968, page 18) in a 100 ml round bottomed flask equipped with magnetic stirrer and an air condenser was added, under nitrogen, 1.46 g (10 mmol) of di-t-butyl peroxide. The mixture was heated at 145° C under nitrogen overnight (> 12 hours). The reaction mixture was fractionally distilled on a 6 inch Vigreaux column to recover unreacted starting material. The distillate (bp 90°-92° C/15 mm) contained a trace of benzaldehyde (by NMR). The NMR spectrum of the product (3.2 g, 8.9 mmol, 89%) was consistent with a 1:1 meso:dl mixture of the bis-trimethylsilylethers of dihydrobenzoin. The product was treated with sodium hydroxide in ethanol to cleave it to dihydrobenzoin. GLC analysis on the isolated dihydrobenzoin (6 foot × ⅛ inch 3% SE-30 on Chrom. W, 140°-200° C at 4°/min) showed that it consisted of a 1:1 mixture of meso and dl diastereomers.

EXAMPLE 6

Methoxy-t-butyldimethylsilane was prepared by using the same procedure as in Example 1 and substituting chloro-t-butyldimethylsilane for chlorotrimethylsilane.

EXAMPLE 7

Coupling of methoxy-t-butyldimethylsilane. To a 20 ml Parr stirred autoclave was added 5.0 g (34 mmol) of methoxy-t-butyldimethylsilane (as produced in Example 6) and 0.5 g (3.4 mmol) of di-t-butylperoxide. The autoclave was stirred at 145° C for 23 hours. The product mixture was distilled on a 6 inch helix-packed column to recover unreacted starting material. The product ethyleneglycol-bis-(t-butyldimethylsilyl)ether was distilled on a short path still, bp 61° C/85 mm.

EXAMPLE 8

In another run, methoxy-t-butyldimethylsilane (15.7 g, 108 mmol) and di-t-butylperoxide (1.58 g, 10.8 mmol) were heated at 145° C in a stainless steel bomb for 16 hours. After methanolysis of the reaction product, the yield of ethylene glycol was 26.9 mg (0.43 mmol, 4%).

In the same manner as in the foregoing examples, other primary alcohols which can be coupled to form higher molecular weight vicinal glycols by employing a trialkylsilyl protecting group on the hydroxyl position of the primary alcohol and heating at an elevated temperature in the presence of an organic peroxide are, for example, aliphatic alcohols and aralkyl alcohols having up to about 10 carbon atoms in the molecule such as n-butyl alcohol, n-hexyl alcohol, n-octyl alcohol, n-decyl alcohol, phenylethyl alcohol and cinnamyl alcohol.

Still other examples and various modifications of the illustrative examples will be apparent to the person skilled in the art after reading the foregoing disclosure without departing from the spirit and scope of the invention. It is intended that all such further examples and modifications be included within the scope of the claims appended hereto.

What is claimed is:

1. In the process of coupling relatively low molecular weight primary alcohols to form relatively higher molecular weight vicinal glycols, the improvement comprising employing a trialkylsilyl protecting group on the hydroxyl position of said low molecular weight primary alcohol during said coupling reaction.

2. The process of claim 1 in which each alkyl in the trialkylsilyl protecting group contains from one to about 4 carbon atoms.

3. The process of claim 2 in which the trialkylsilyl group is trimethylsilyl.

4. The process of claim 2 in which the trialkylsilyl groups is t-butyldimethylsilyl.

5. The process of claim 1 in which the relatively low molecular weight primary alcohol is methanol.

6. The process of claim 1 in which the relatively low molecular weight primary alcohol is ethanol.

7. The process of claim 1 in which the relatively low molecular weight primary alcohol is benzyl alcohol.

8. The process of claim 1 in which the coupling reaction is facilitated by heating at an elevated temperature in the presence of an organic peroxide.

9. The process of claim 8 in which the reaction temperature ranges from about 110° C to about 180° C.

10. The process of claim 8 in which the organic peroxide is di-t-butyl peroxide.

11. The process of preparing ethylene glycol comprising coupling 2 molecules of methoxytrialkylsilane to form 1,2-bis(trialkylsiloxy)ethane followed by methanolysis thereof to yield ethylene glycol.

12. The process of claim 11 in which each alkyl in the methoxytrialkylsilane is methyl and the coupling is facilitated by heating at an elevated temperature in the presence of an organic peroxide.

13. The process of claim 12 in which the reaction temperature ranges from about 110° C to about 180° C and the organic peroxide is di-t-butyl peroxide.

14. The process of claim 11 in which the trialkylsilyl group in the methoxytrialkylsilane is t-butyldimethylsilyl and the coupling is facilitated by heating at an elevated temperature in the presence of an organic peroxide.

15. The process of claim 14 in which the reaction temperature ranges from about 110° C to about 180° C and the organic peroxide is di-t-butyl peroxide.

16. The process of preparing glycerol comprising coupling 3 molecules of methoxytrialkylsilane to form 1,2,3-tris(trialkylsiloxy)propane followed by methanolysis thereof to yield glycerol.

17. The process of claim 16 in which each alkyl in the methoxytrialkylsilane is methyl and the coupling is facilitated by heating at an elevated temperature in the presence of an organic peroxide.

18. The process of claim 17 in which the reaction temperature ranges from about 110° C to about 180° C and the organic peroxide is di-t-butyl peroxide.

* * * * *